United States Patent
Meyer (10) Patent No.: US 9,439,577 B2
(45) Date of Patent: Sep. 13, 2016

(54) NON-INVASIVE METHODS FOR DETERMINING CARDIAC OUTPUT

(71) Applicant: The University of Vermont and State Agricultural College, Burlington, VT (US)

(72) Inventor: Markus Meyer, Williston, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 14/387,962

(22) PCT Filed: Mar. 13, 2013

(86) PCT No.: PCT/US2013/030740
§ 371 (c)(1),
(2) Date: Sep. 25, 2014

(87) PCT Pub. No.: WO2013/148180
PCT Pub. Date: Oct. 3, 2013

(65) Prior Publication Data
US 2015/0080687 A1    Mar. 19, 2015

Related U.S. Application Data

(60) Provisional application No. 61/616,140, filed on Mar. 27, 2012.

(51) Int. Cl.
*A61B 5/02*    (2006.01)
*A61B 5/029*    (2006.01)
(Continued)

(52) U.S. Cl.
CPC ............. *A61B 5/029* (2013.01); *A61B 5/0205* (2013.01); *A61B 5/14552* (2013.01);
(Continued)

(58) Field of Classification Search
CPC .......... A61B 5/02028; A61B 5/02416; A61B 5/0295; A61B 5/1455; A61B 5/6813; A61B 5/029; A61B 5/0205
See application file for complete search history.

(56) References Cited

U.S. PATENT DOCUMENTS

D333,015 S    2/1993    Farmer et al.
D347,494 S    5/1994    Mustelier, Jr.
(Continued)

FOREIGN PATENT DOCUMENTS

WO    WO 99/53834 A1    10/1999
WO    WO 00/67634 A2    11/2000
WO    WO 01/30234 A2    5/2001

OTHER PUBLICATIONS

International Search Report and Written Opinion for International Application No. PCT/US2013/030740 mailed May 27, 2013.
(Continued)

*Primary Examiner* — Robert N Wieland
(74) *Attorney, Agent, or Firm* — Wolf, Greenfield & Sacks, P.C.

(57) ABSTRACT

Cardiac output is measured using a non-invasive method comprised of administering hyperbaric or hypobaric gas to the subject then after a time measuring the resultant changes in central or peripheral oxygen saturation times using a pulse oximeter located at a peripheral body site. Preferably the device is portable and is comprised of a gas cartridge, with one or more doses, and a mouth-piece, a microprocessor for performing the analysis, a pulse oximeter probe and a display for reporting the cardiac output.

22 Claims, 5 Drawing Sheets

(51) Int. Cl.
*A61B 5/0205* (2006.01)
*A61B 5/00* (2006.01)
*A61M 16/06* (2006.01)
*A61M 16/12* (2006.01)
*A61M 16/20* (2006.01)
*A61B 5/1455* (2006.01)

(52) U.S. Cl.
CPC ............ *A61B 5/682* (2013.01); *A61B 5/6816* (2013.01); *A61B 5/6822* (2013.01); *A61B 5/6826* (2013.01); *A61B 5/6831* (2013.01); *A61B 5/6833* (2013.01); *A61B 5/6838* (2013.01); *A61B 5/7278* (2013.01); *A61B 5/7282* (2013.01); *A61M 16/06* (2013.01); *A61M 16/12* (2013.01); *A61M 16/20* (2013.01); *A61B 5/14551* (2013.01); *A61M 2202/025* (2013.01); *A61M 2202/0208* (2013.01); *A61M 2202/0283* (2013.01); *A61M 2205/502* (2013.01)

(56) References Cited

U.S. PATENT DOCUMENTS

| | | | |
|---|---|---|---|
| D351,226 S | 10/1994 | Parvatharaj | |
| 5,474,060 A | 12/1995 | Evans | |
| 5,570,689 A | 11/1996 | Starr et al. | |
| 5,676,133 A | 10/1997 | Hickle et al. | |
| 5,701,886 A | 12/1997 | Ryatt | |
| 5,842,470 A | 12/1998 | Ruben | |
| 5,909,732 A | 6/1999 | Diesel et al. | |
| 5,918,598 A | 7/1999 | Belfer et al. | |
| 6,092,521 A | 7/2000 | Miura | |
| D431,077 S | 9/2000 | McGinnis et al. | |
| 6,186,142 B1 | 2/2001 | Schmidt et al. | |
| 6,196,223 B1 | 3/2001 | Belfer et al. | |
| 6,386,198 B1 | 5/2002 | Rugless | |
| 6,517,496 B1 | 2/2003 | Mault | |
| 6,871,648 B1 | 3/2005 | Winekoff | |
| 7,152,602 B2 | 12/2006 | Bateman et al. | |
| 7,559,323 B2 | 7/2009 | Hacke et al. | |
| 7,686,018 B2 | 3/2010 | Cerbini | |
| 8,100,126 B2 | 1/2012 | McAuley et al. | |
| 8,146,594 B2 | 4/2012 | Bostock et al. | |
| 2003/0135124 A1* | 7/2003 | Russell .............. | A61B 5/02007 600/500 |
| 2003/0167016 A1* | 9/2003 | Mault ................... | A61B 5/029 600/529 |
| 2005/0245833 A1 | 11/2005 | Kline | |
| 2006/0173258 A1* | 8/2006 | Kobayashi ........... | A61B 5/0059 600/323 |
| 2007/0078357 A1* | 4/2007 | Kline .................. | A61B 5/0836 600/532 |
| 2009/0318787 A1 | 12/2009 | Aoyagi et al. | |
| 2010/0191080 A1* | 7/2010 | Mills .................. | A61B 5/02028 600/323 |
| 2012/0310059 A1* | 12/2012 | Pinto ................... | G06F 19/3418 600/323 |
| 2013/0060110 A1* | 3/2013 | Lynn .................... | A61B 7/003 600/324 |
| 2013/0123592 A1* | 5/2013 | Rule .................... | A61B 5/029 600/323 |
| 2014/0180026 A1* | 6/2014 | Melker ................ | A61B 5/0873 600/301 |
| 2015/0045686 A1* | 2/2015 | Lynn .................... | A61B 5/00 600/531 |

OTHER PUBLICATIONS

International Preliminary Report on Patentability for International Application No. PCT/US2013/030740 mailed Oct. 9, 2014.
Denslow et al., Pulse oximetry-gated acquisition of cardiac MR images in patients with congenital cardiac abnormalities. AJR Am J Roentgenol. Apr. 1993;160(4):831-3.
Kasravi et al., A noninvasive method for estimating cardiac output using lung to finger circulation time of oxygen. Am J Cardiol. Oct. 1, 1998;82(7):915-7.

* cited by examiner

Figure 5

US 9,439,577 B2

NON-INVASIVE METHODS FOR DETERMINING CARDIAC OUTPUT

RELATED APPLICATIONS

This application is a national stage filing under U.S.C. §371 of PCT International Application PCT/US2013/030740 filed Mar. 13, 2013, which claims the priority benefit under 35 U.S.C. §119(e) of U.S. Provisional Application No. 61/616,140, entitled "NON-INVASIVE METHODS FOR DETERMINING CARDIAC OUTPUT," filed Mar. 27, 2012, the disclosure of which is incorporated herein by reference in its entirety.

FIELD OF THE INVENTION

The present invention relates generally to devices suitable for the analysis of cardiac output, and method of performing such a method in a non-invasive manner.

BACKGROUND OF INVENTION

Cardiac output is a an important parameter in assessing the health or disease state of a subject. For instance, a significantly decreased cardiac output can be predictive of heart failure or the presence of embolisms. Increased cardiac outputs are also found in states of sepsis. Many existing methods that are effective for determining cardiac output have the disadvantage of being invasive. Measurements of cardiac output are commonly made by invasive heart catheterization or by using time-consuming and expensive methodologies such as echocardiography or magnetic resonance imaging. Historically cardiac outputs were determined by the measurement of circulation times. To achieve this dye was injected into the vascular system and the time that the dye took to appear in an unrelated body site was measured.

SUMMARY OF THE INVENTION

Methods and related products for assessing cardiac output in a manner that is highly effective and non-invasive are provided according to the invention. In some aspects the invention is a non-invasive method for measuring cardiac output by administering to a subject a hyperbaric or hypobaric gas and measuring changes in central or peripheral oxygen saturation with time using pulse oximetry at a peripheral body site representative of central circulation times. In some embodiments a peripheral body site representative of central circulation times is the neck, face, skin, lips, tongue or ear lobe.

In other embodiments the measurement of cardiac output provides a reading consistent with normal status, heart failure, or sepsis.

The changes in oxygen saturation with time may be central circulation times of more than 15 seconds for heart failure, 8-15 seconds for normal status, or less than 8 seconds for sepsis with increased cardiac output, in some embodiments.

In some embodiments the peripheral body site representative of central circulation times is a finger.

The hyperbaric or hypobaric gas in some embodiments is selected from the group consisting of nitrogen, oxygen, helium, argon, nitrous oxide, or any mixtures or combinations thereof. The gas may be, for instance, 100% of the gas that is delivered to the subject. Alternatively the gas may be 70%, 75%, 80%, 85%, 90%, 95%, 96%, 97%, 98%, or 99%% of the gas that is delivered to the subject and wherein the remaining percentage is oxygen.

In other embodiments the device includes a gas delivery system that has a safety valve.

In yet other embodiments the pulse oximetry is achieved using a pulse oximeter having a probe, a housing, and a microprocessor. The probe may have a photoemitter and a photodetector and/or may be in the form of a clip, a sleeve, or an adhesive bandage.

In yet other embodiments the subject is a patient being treated by medical personnel. In other embodiments the subject is using the device on their own.

The invention in other aspects is a device having a pulse oximeter capable of detecting oxygen saturation from central circulation and having an output signal component for transferring the value of oxygen saturation to a processor, wherein the processor is programmed to calculate cardiac output based on the oxygen saturation values.

In some embodiments the device includes a gas delivery system that has a safety valve.

In other embodiments the pulse oximeter has a probe, a housing, and a microprocessor. The probe in some embodiments has a photoemitter and a photodetector. The probe may be in the form of a clip, a sleeve, or an adhesive bandage.

The housing in some embodiments includes a read-out display.

In other embodiments the processor produces a processed signal that is delivered to a computer.

In some embodiments the device includes several discreet components including a gas delivery system for delivering the gas, a free standing probe, and a microprocessor. The gas delivery system may be a mask. Optionally, the gas delivery system is connected to a continuous supply of one or more gases. In other embodiments the gas delivery system is connected to a gas cartridge.

The free standing probe in some embodiments is connected wirelessly to a data processing unit. In other embodiments the free standing probe is connected via wire to a data processing unit.

A portable device, is provided in other aspects of the invention. The device has a housing comprising a gas cartridge housing one or more doses of a gas, a mouthpiece for delivering the gas to the subject, a probe for measuring the gas in the blood, a microprocessor for processor for displaying the signal and a read-out screen for displaying the results of the analysis.

In some embodiments one or more of: the gas cartridge, the mouthpiece, the probe, the microprocessor or the read-out screen is attached directly to the housing. In other embodiments each of the gas cartridge, the mouthpiece, the probe, the microprocessor or the read-out screen is attached directly to the housing. In other embodiments one or more of: the gas cartridge, the mouthpiece, the probe, the microprocessor or the read-out screen is attached to the housing indirectly through a wire or tube or other connection device.

The gas cartridge may be a single use cartridge or a multiple use cartridge.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

Aspects of the invention are described in connection with the following illustrative non-limiting drawings in which like numerals reference like elements, and wherein.

DETAILED DESCRIPTION

The invention in some aspects provides a new method for assessing cardiac output that is highly effective and non-invasive. Because the method is rapid and non-invasive it can be used in a variety of situations where a quick determination of cardiac output is essential. For instance, when a subject is having symptoms of shortness of breath it is important to determine whether the subject is having heart failure or some other condition. Cardiac output refers to the amount of blood that is pumped every minute. If available, knowledge of the cardiac output is extremely helpful in the management of seriously ill patients. Historically cardiac output was measured by recording travel times of an intravenously injected agent until it appeared in the arteries. This measurement is called circulation time. Despite being very accurate and reproducible circulation times have fallen out of favor because the test is time consuming and inconvenient as it requires the analysis of many blood samples.

The methods of the invention utilize pulse oximetry to assess cardiac output. The methods are designed such that pulse oximetry can be used to measure circulation times in a non-invasive manner without using injected agents or the need for blood samples. A pulse oximeter measures blood oxygen levels through the skin. In order to achieve this the oxygen concentration of the inhaled air is changed to either hyperbaric or hypobaric conditions. The time it takes to change the oxygen saturation at a peripheral site is directly related to cardiac output. Thus, the invention involves the induction of brief changes in blood oxygen levels by breathing air with an altered oxygen content. The time it takes to detect the temporary change in oxygen level to occur at a peripheral site, which is referred to herein as the oxygen transit time, for example in a finger, is directly related to cardiac output. The functionality of the invention has been demonstrated in human subjects.

Figure 1:
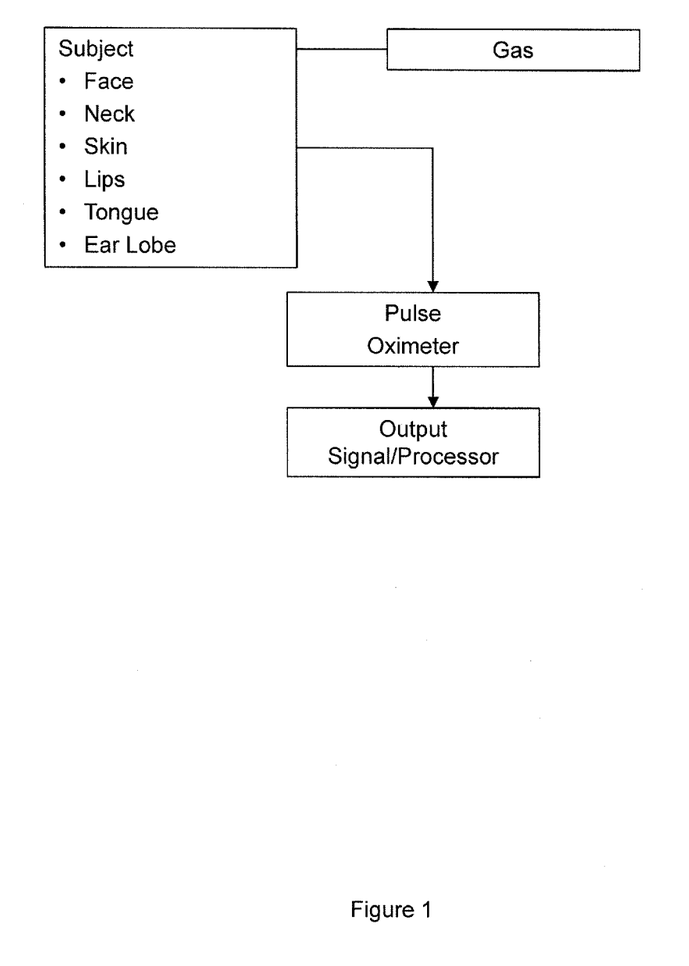
FIG. 1 is a flow chart showing exemplary processes of the invention.

The methods of the invention are depicted schematically in the flow chart shown in FIG. 1. In the Figure, the hyperbaric or hypobaric gas is administered to a subject. The subject is linked to a pulse oximeter through a peripheral probe connected to a body part that has central circulation exposed enough that a central circulation time can be measured. Measurements of arterial partial pressure and oxygen saturation are made and transferred to a processor that collects and processes the information to provide a patient read-out.

Thus, in the methods of the invention the subject is initially exposed to a hyperbaric or hypobaric gas. A hyperbaric or hypobaric gas, as used herein, refers to a gas having greater than normal partial pressure of oxygen or lower than normal partial pressure of oxygen or weight; of gases under greater than atmospheric pressure, or of a solution of greater specific gravity than another used as a reference standard. In some embodiments, the hyperbaric or hypobaric gas is nitrogen, oxygen, helium, argon, nitrous oxide, or any mixtures or combinations thereof. The gas may be 100% of the gas that is delivered to the patient or it may be less, for instance, 70%, 75%, 80%, 85%, 90%, 95%, 96%, 97%, 98%, or 99%. In some embodiments the hyperbaric or hypobaric gas is 100% nitrogen or 100% oxygen or any mixtures of the two. In other embodiments, the hyperbaric or hypobaric gas is a helium/oxygen mixture. Helium and oxygen mixtures, for example, are available in ratios of 80:20, 70:30, and 60:40 (helium:oxygen).

The gas may be delivered to the subject using known methods in the art. For instance the gas may be delivered to the subject from a gas storage device through a tube and a face mask, worn by the subject, into the subject's respiratory system. Alternatively the gas may be delivered from a gas delivering cartridge through a mouthpiece. The gas delivery system may optionally include metered controls for delivering a preset amount of gas to the subject. Alternatively the gas delivery device may be controlled manually with the amount of gas metered based on time of administration. Other methods of delivering gases to subjects are known in the art and are useful according to the methods and devices of the invention.

The gas delivery system may include and be controlled by a safety valve. The safety valve allows a controlled amount of gas to be delivered to the subject. It is desirable to only deliver a controlled amount of gas so that a subject does not receive toxic doses of a gas. This type of system can be easily integrated into oxygen delivery systems in hospitals and medical offices. Upon taking a breath of the altered air mixture a timer is started that records the oxygen transit times to various body sites.

The gas delivery system used in the invention is a component that that can deliver a gas to a human subject. Gas delivery systems are known in the art and include for instance, masks, mouthpieces, inhalers etc. A delivery system such as a mask may include a mask body having a rim for contacting the patient's face and an interior space configured to surround and enclose the patient's nose and mouth. The mask may include a gas diffuser structure projecting through the mask body into the interior space. The gas diffuser structure may include a gas delivery tube which may have an inlet within the tube for communication with a source of pressurized gas and an outlet from the tube. A flow of gas entering the mask forms a burst of enriched gas at the patient's nose and mouth region, thereby permitting a relatively high gas content to be delivered to the patient in a rapid time frame. The mask may include the safety valve for carefully controlling the amount and type of gas that flows into the subject.

Exemplary types of masks include but are not limited to simple masks, non-rebreathing masks, airway mask breathing units (AMBU), and demand/resuscitator valves, such as those commercially available from life medical. Some masks include sensors or regulators for indicating or confirming exactly how much the patient is inhaling per volume. Examples of such masks include ALPS FaceMask available from Mountain High; Anesthesia oxygen masks; Oxygen helmets; Mask retention systems; Reusable cuffed masks, and Laryngeal masks. Masks are also described in, for instance, U.S. Pat. No. 5,474,060, U.S. Pat. No. 5,570,689, U.S. Pat. No. 5,676,133, U.S. Pat. No. 5,701,886, U.S. Pat. No. 5,842,470, U.S. Pat. No. 5,909,732, U.S. Pat. No. 5,918,598, U.S. Pat. No. 6,092,521, U.S. Pat. No. 6,196,223, U.S. Pat. No. 6,386,198, U.S. Pat. No. 6,871,648, U.S. Pat. No. 7,152,602, U.S. Pat. No. 7,559,323, U.S. Pat. No. 7,686,018, U.S. Pat. No. 8,100,126, U.S. Pat. No. 8,146,594, U.S. D333015, U.S. D347494, U.S. D351226, and U.S. D431077.

The subject is also connected to a pulse oximeter, such that once the subject has breathed the gas any changes in oxygen saturation can be measured. A pulse oximeter is a device that measures the arterial oxygen saturation of hemoglobin. A probe portion of the pulse oximeter is attached to a subject. The probe is designed to measure the absorption of light at two different wavelengths by hemoglobin depending on the degree of oxygenation of the hemoglobin. Then a signal is detected as a result of the changing volume of arterial blood with each pulse beat. The signals are transmitted from the probe to the housing portion of the oximeter, to a microprocessor contained therein.

A probe is a sensor that detects signals of different wavelengths. Typically the probe has a photoemitter that is capable of emitting light, often at more than one wavelength and a photodetector that detects the signal. The absorbance value obtained by the photodetector is used to analyze the gas within the blood. The probe may be designed to attach to the skin of a subject. For instance, the probe may be in the form of a clip, a sleeve, or an adhesive bandage.

The pulse oximeter measures the oxygen saturation of hemoglobin in arterial blood. This refers to a measure of the average amount of oxygen bound to each hemoglobin molecule. The percentage saturation typically is given as a digital readout together but any type of read-out is envisioned by the invention. The pulse rate is typically measured in beats per minute, averaged over 5 to 20 seconds.

A pulse oximeter typically includes a peripheral probe and a microprocessor unit, displaying a waveform, the oxygen saturation and the pulse rate. The probe is placed on a peripheral part of the body such as the neck, face or an ear lobe. The probe typically includes at least two light emitting diodes (LED's), one in the visible red spectrum (660 nm) and the other in the infrared spectrum (940 nm). The light is passed through the tissues to a photodetector. During passage through the tissues, some light is absorbed by blood and soft tissues depending on the concentration of hemoglobin. The amount of light absorption at each light frequency depends on the degree of oxygenation of hemoglobin within the tissues.

The relationship between the arterial partial pressure of oxygen ($PaO_2$) and the oxygen saturation can be described graphically using a hemoglobin-oxygen dissociation curve. A hemoglobin-oxygen dissociation curve typically has a sigmoid shape, which is shifted to the left or right by various conditions including the administration of hyperbaric or hypobaric gases and the disease state of a subject.

A subject as used herein is preferably a human subject, but may also include non-human animals in some embodiments. In some embodiments the human subject is a patient being treated by medical personnel. In other embodiments a human subject uses the device without the assistance of a medical personnel. For instance, the subject may use the device themselves. The probe of the pulse oximeter is attached to a peripheral body site of the subject. The peripheral body site is one that is capable of providing an output of central circulation times. Some examples of preferred body sites useful according to the invention include the neck, finger, face, skin, lips, tongue or ear lobe. In some embodiments the fingertip is used for detection. In other embodiments the fingertip is not used.

Figure 2:
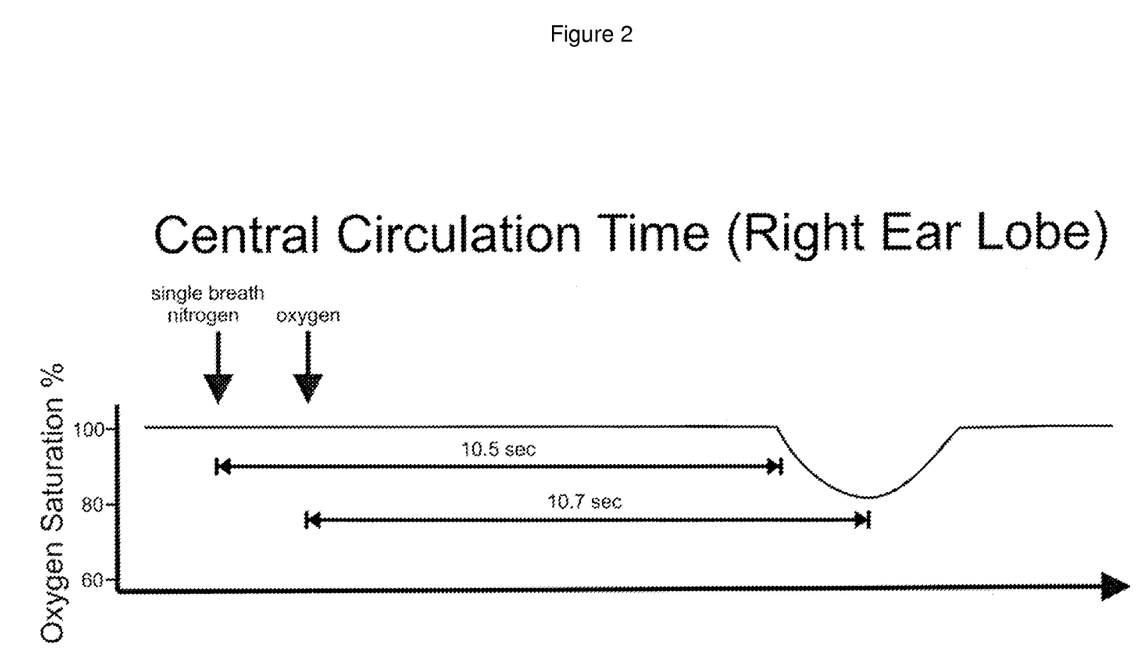
FIG. 2 is a graph depicting the % oxygen saturation over time in the methods of the invention.
Figure 3:
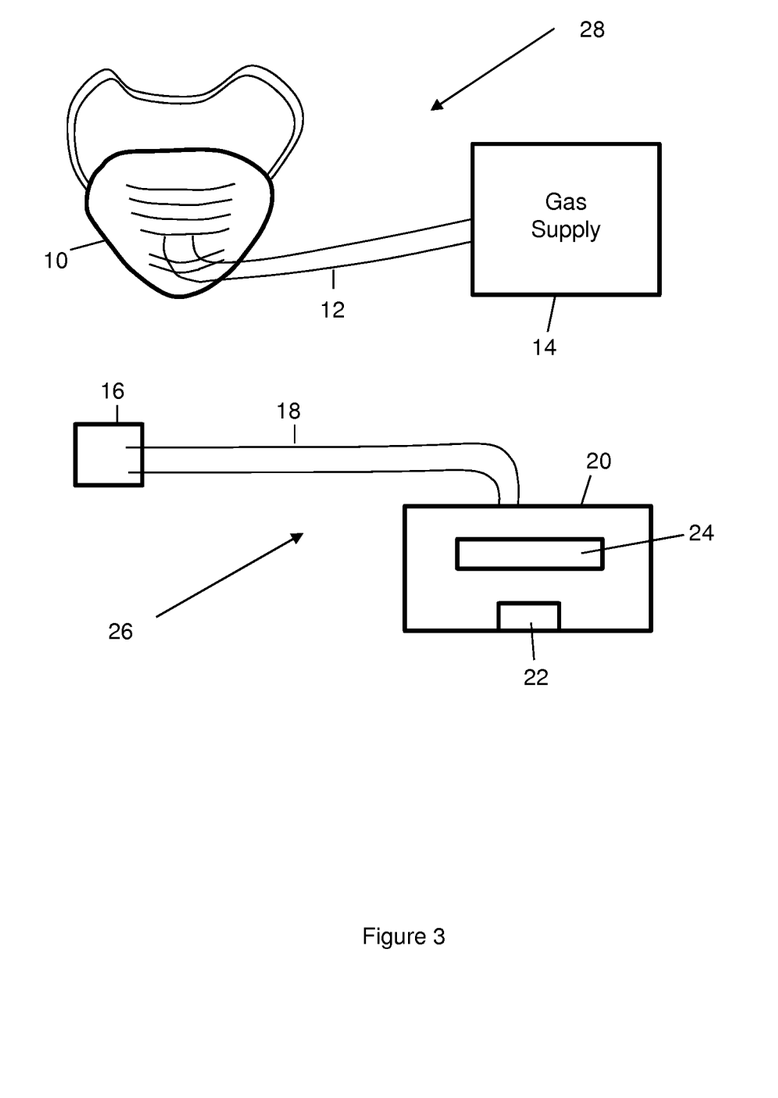
FIG. 3 is a schematic of the device of the invention.

FIGS. 2 and 3 depict illustrative embodiments of the methods and devices incorporating aspects of the present invention. The pulse oximeter 26 shown in FIG. 3 includes a housing 20, having a microprocessor 22 and a read-out display 24. The housing is also connected to a set of wires 18 that lead to one or more probes 16. The probes can be attached to the subjects body and may optionally include a mechanism for attachment to the subject. When a signal is produced and detected by the probe 16, the signal is sent through the wires 18 to the housing 24 wherein it is processed by the microprocessor. The processed signal may be displayed as a read-out on the display 24 or transferred to another component for the delivery of the information to a user. For instance the processed signal may also be delivered to a computer which further processes and/or presents the information.

Exemplary types of pulse oximeters include but are not limited to handheld oximeters, tabletop oximeters, fingertip pulse oximeters, sport oximeters, pediatric oximeters and bedside pulse oximeters. wristband pulse oximeters, and ECG Synchronized Pulse Oximeters. ECG Synchronized Pulse Oximeters, for instance, are able to eliminate errors due to the motion of the patient.

Examples of commercially available pulse oximeters include but are not limited to GE Ohmeda TuffSat Handheld Oximeter, Smiths Medical SPECTRO2, GE Ohmeda TruSat Tabletop, GE Oximeter Model #3500, Smiths Medical Hand-Held SPECTRO2, Smiths Medical BCI, Digit Finger Oximeter Premium—MEDLINE BCE300C53, Autocorr Digital Pulse Oximeter, 3304 Bedside Pulse Oximeter, Finger Tip Pulse Oximeter Premium—MEDLINE BCE300C61, PROBE, FINGER, CHOICE OXIMETER, MD-300-C2 by Carefus, HCSFSATSPORT OXIMETER, PULSE, AAA BATTERY, NONRX (Medline), OxySure Pulse Oximeter Premium, Pulse Oximeters Digit Finger Oximeter-3420Y (Smiths Medical), Clinical Guard OT-99 Finger Pulse Oximeter, Fingertip Oximeter Entry Level Octive Tech 300CEN, OLED CMS50D Fingertip Pulse Oximeter, Finger Pulse Oximeter OctiveTech 300C, Pulse Oximeter OctiveTech 300CSE—Heavy Duty, OLED Finger Pulse Oximeter OctiveTech 300D, Finger Pulse Oximeter OctiveTech 300PRO, CMS-50E OLED Fingertip Pulse Oximeter, CMS 50QA Pediatric Finger Pulse Oximeter—LED, Pediatric Pulse Oximeter OctiveTech 300PN, CMS 50QB Pediatric Finger Pulse Oximeter—OLED, CMS-50E OLED Fingertip Pulse Oximeter, CMS 50QA Pediatric Finger Pulse Oximeter, Pediatric Pulse Oximeter OctiveTech 300PN, CMS 50QB Pediatric Finger Pulse Oximeter, Nonin GO2 Achieve Fingertip Pulse Oximeter, Nonin 9590 Onyx Vantage Finger Pulse Oximeter, BCI Digit Finger Pulse Oximeter, Handheld Pulse Oximeter OctiveTech 300AH, CMS CONTEC PM-50 NIBP/SPO2 Blood Pressure Monitor, BCI 3301 Hand Held Pulse Oximeter, BCI SPECTRO2 10 Pulse Oximeter, Handheld Pulse Oximeter OctiveTech 300AH, Multi-user CMS-60F Handheld Finger Pulse Oximeter, Palm Size CMS-60C Pulse Oximeter with software, Wristband Pulse Oximeter CMS-50F with software The pulse oximetry process involves the transmission of light through tissue and the detection of signaling resulting from emitted light. The beams of light are applied and detected by a sensor containing light emitting diodes and a photodetector. An oximeter computes saturation depending upon the relative magnitudes of the AC components of the two absorption waveforms or plethysmographs. These AC components are, in general, small compared to the magnitude of the total waveform (AC+DC components) representative of total absorption present.

Several pulse oximeters involve optimized systems for measuring oxygen even when the body is in motion. For example in some systems the synchronization of the plethysmographs with an ECG signal. The ECG signal is used to determine the period of the plethysmographs and to guide the measurement of the peak and valley values from which the AC components and, ultimately, oxygen saturation are computed. By fixing the temporal location of the peak and valley sampling relative to the R-wave of the ECG, this solution eliminates the error introduced by searching for peaks in the presence of artifact.

Microprocessors in pulse oximeters typically can select the absorbance of the pulsatile fraction of blood arising from the arterial blood, from constant absorbance due to non-pulsatile venous or capillary blood and other tissue pigments. Many advanced microprocessors have been developed which can provide very reliable readings. Any of these microprocessors are useful according to the invention. Examples of software for use in the microprocessor include but are not limited to MedView Data Management Software for Oximetry and nVISION® oximetry data management software. Examples of Microprocessors include but are not limited to TI's TMS320C5515 DSP Evaluation Module together with TI's pulse oximeter analog front-end module.

FIG. 2 shows a read-out from a pulse oximeter. In the Example shown a subject took a single breath of nitrogen followed by oxygen and the percent oxygen saturation was measured.

Also shown in FIG. 3 is the mechanism for delivering hyperbaric or hypobaric gases to a subject. A gas supply 14 is shown as connected to a gas delivery tube 12. The gas delivery tube is connected to a face mask or mouthpiece 10 which may be placed on the subject's face. Although FIG. 3 depicts the device as two separate parts the device may actually be configured as a single component where one or more housings are configured to deliver a gas supply and collect information from the probe placed on the subject's body.

The device may be configured in a number of ways. In some instances the device may be composed of several discreet components which can be used in conjunction with one another to achieve the methods of the invention. For instance, the device may be composed of a mask for delivering the gas which may or may not be connected to a continuous supply of one or more gases and a free standing probe connected wirelessly or via wire to a data processing unit. For example in a medical facility each of the components may be free standing such that they can be used in conjunction with other medical equipment. Portable devices, single use devices and/or single component devices are also envisioned according to the invention.

A portable device is one which is smaller in size than instrumentation typically used in a medical facility and which can easily be transported on or by a human subject. Portable devices may be housed in or removal attached to a carrier or a wheeled device.

A single component device is a device in which all the necessary components for practicing the methods are found in a single unit or housing. The single component device, for instance, may be a hand held device which includes a gas cartridge housing one or more doses of a gas, a mouthpiece for delivering the gas to the subject, a probe for measuring the gas in the blood, a microprocessor for processor for displaying the signal and a read-out screen for displaying the results of the analysis. Any of the components may directly incorporated into the single housing or attached via a wire or tube or other connection device to the housing.

A single use device is one which is designed to be used a single time. These include devices in which the entire device is used a single time and then disposed of as well as devices having some basic reusable parts and one or more single use components. For example a single use device may include a basic housing containing a microprocessor and display component which can be reused. Such a device might have an area for attachment of a single use gas cartridge, with or without a single use mouthpiece for delivering the gas to the subject. The mouthpiece may also be non-disposable and be part of the housing. The device may also have a single use probe that can be replaced.

Figure 4:
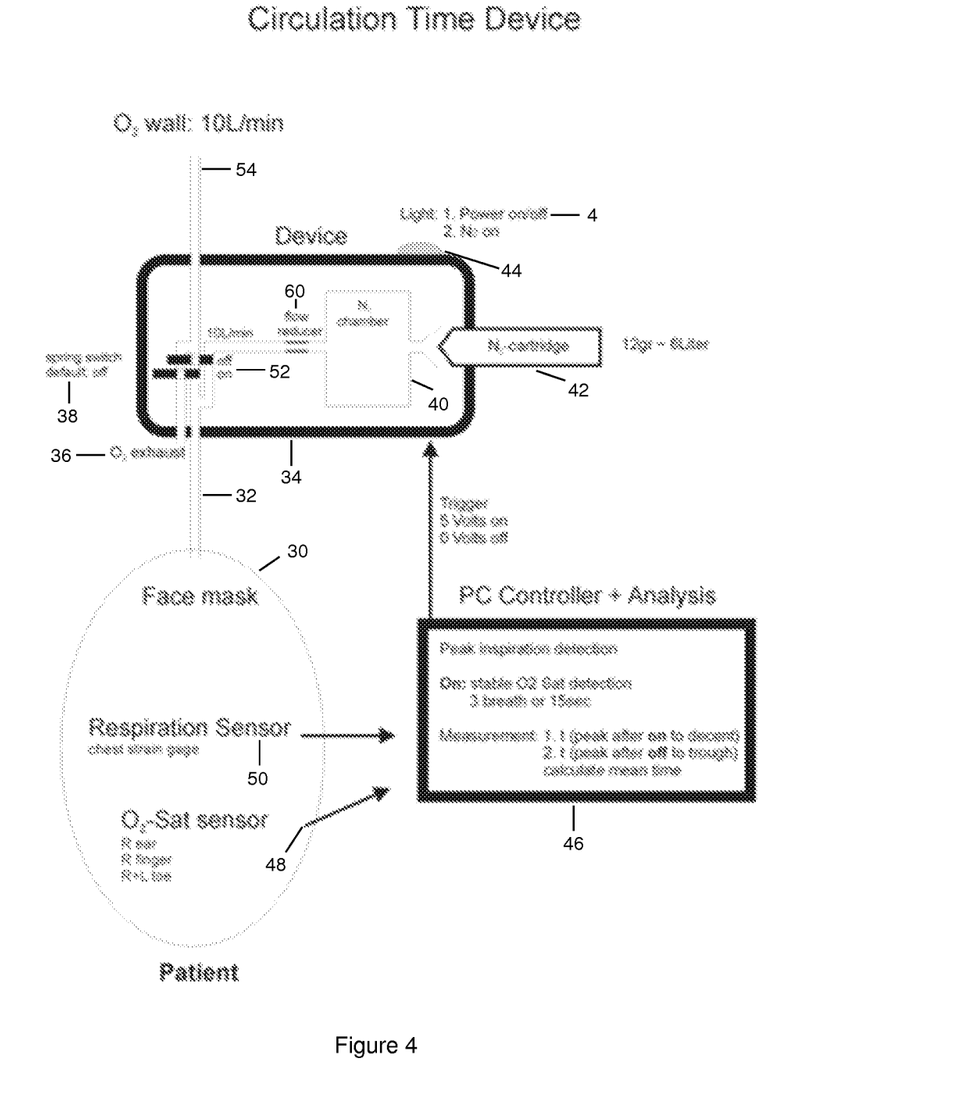
FIG. 4 is a diagram depicting elements and functionality of a device of the invention.

FIG. 4 shows a detailed schematic of a device and method of the invention. In the Figure, a face mask, 30, is positioned on the patient's face. The face mask, 30, is connected by tubing, 32, to a device for delivering gas, 34, to the face mask. The device for delivering gas, 34, includes an on-off switch, 44, for controlling the power on the device. A gas cartridge, 42, for delivering, for example, nitrogen, into a gas chamber, 40. The gas chamber, 40, is connected through tubes, including a flow reducer, 60, and having an on-off switch, 52, and a spring switch with a default off, 38. The gas is delivered through the tubes from the gas chamber to the face mask. The device may also be connected to an oxygen source, such as an oxygen wall, 54, for delivery of the oxygen after the nitrogen burst. An oxygen exhaust tube, 36, allows gas to be released from the device. The device also includes a microprocessor, 46, which can include a respiration sensor, 50, and an oxygen saturation sensor, 48. The device may be referred to herein as CorFlo.

The CorFlo device is used for any purpose when it is desirable to measure or assess cardiac output. It is often desirable to measure cardiac output in a medical setting. For instance the ability to monitor cardiac output under acute conditions in an emergency room setting is desirable. It is also useful to measure cardiac output in a diagnostic or clinical setting. Due to the portability of the device of the invention the measurement of cardiac output may now be expanded to routine uses. For instance, a user may monitor their own cardiac output under various conditions away from a medical setting, for instance during exercise or under any other conditions in which it is useful to have this measurement.

The methods of the invention may also be used to determine the distribution of blood to different vascular beds, peripheral vascular disease and endothelial function.

Other configurations will be easily envisioned by the skilled artisan and are within the scope of the invention.

The present invention is further illustrated by the following Examples, which are not to be construed as limiting the scope of the invention in any manner.

EXAMPLES

Example 1

One breath of nitrogen gas was inhaled by a human subject, at which a stop watch was started. This was followed by a breath of oxygen gas. The time until the oxygenation decreased at the right earlobe reflects central circulation time, as shown in FIG. 2. This time was identical to the time it took from taking a breath of oxygen to the lowest point of oxygen saturation that was followed in a normalization in oxygen saturation. Both times are a reflection of the circulation time.

Example 2

Figure 5:
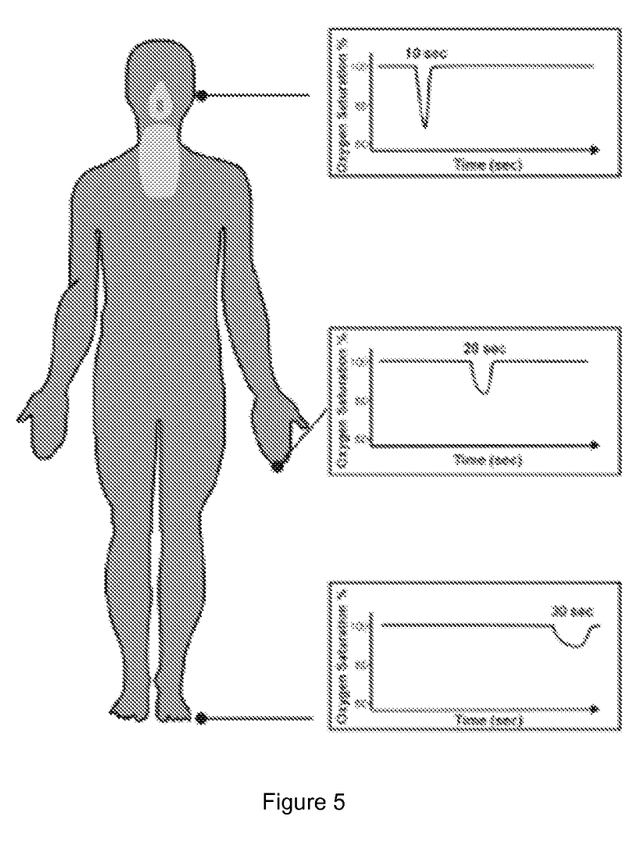
FIG. 5 is a diagram and a set of graphs. The graphs depict data output measured at body sites indicated by arrows to the diagram.

A human subject was administered a single breath of nitrogen gas through a proprietary delivery system of the invention, having a safety valve. Upon taking a breath of the altered air mixture a timer was started and the oxygen transit times to various body sites was recorded. The change in blood oxygen level was measured using a standard pulse oximeter as an earlobe, a fingertip and a toe. As shown in FIG. 5, oxygen transit times were recorded at 10 seconds (earlobe), 20 seconds (fingertip), and 30 seconds (toe). The measurements were easy to detect and highly reproducible. The data will provide a cardiac output value.

While the invention has been described with reference to various illustrative embodiments and examples, the invention is not limited to the embodiments described. It is evident that many alternatives, modifications and variations of the embodiments described will be apparent to those of ordinary skill in the art. Accordingly, embodiments of the invention as set forth herein are intended to be illustrative, and not limiting the scope of the invention. Various changes may be made without departing from the scope of the invention.

What is claimed is:

1. A non-invasive method for measuring cardiac output, comprising
administering to a subject a hyperbaric or hypobaric gas and measuring changes in central or peripheral oxygen saturation with time using pulse oximetry at a peripheral body site representative of central circulation times, wherein time is measured from the time of administration of the hyperbaric or hypobaric gas to the measurement taken at the peripheral body site.

2. The method of claim 1, wherein the measurement of cardiac output provides an indication of heart failure.

3. The method of claim 2, wherein the changes in oxygen saturation with time are central circulation times of more than 15 seconds for heart failure, 8-15 seconds for normal status, or less than 8 seconds for sepsis with increased cardiac output.

4. The method of claim 1, wherein the peripheral body site representative of central circulation times is the face or neck.

5. The method of claim 1, wherein the peripheral body site representative of central circulation times is the skin.

6. The method of claim 1, wherein the peripheral body site representative of central circulation times is the lips.

7. The method of claim 1, wherein the peripheral body site representative of central circulation times is the tongue.

8. The method of claim 1, wherein the peripheral body site representative of central circulation times is ear lobe.

9. The method of claim 1, wherein the peripheral body site representative of central circulation times is a finger.

10. The method of claim 1, wherein the hyperbaric or hypobaric gas is selected from the group consisting of nitrogen, oxygen, helium, argon, nitrous oxide, or any mixtures or combinations thereof.

11. The method of claim 10, wherein the gas is 100% of the gas that is delivered to the subject.

12. The method of claim 10, wherein the gas is 70%, 75%, 80%, 85%, 90%, 95%, 96%, 97%, 98%, or 99%% of the gas that is delivered to the subject and wherein the remaining percentage is oxygen.

13. The method of claim 1, wherein the device includes a gas delivery system that has a safety valve.

14. The method of claim 1, wherein pulse oximetry is achieved using a pulse oximeter having a probe, a housing, and a microprocessor.

15. The method of claim 14, wherein the probe has a photoemitter and a photodetector.

16. The method of claim 14, wherein the probe is in the form of a clip, a sleeve, or an adhesive bandage.

17. The method of claim 1, wherein subject is a patient being treated by medical personnel.

18. The method of claim 1, wherein the subject is using the device on their own.

19. A device comprising:
a pulse oximeter capable of detecting oxygen saturation from central circulation and having an output signal component for transferring the value of oxygen saturation to a processor, wherein the processor is programmed to calculate cardiac output based on the oxygen saturation values.

20. The device of claim 19, wherein the device includes a gas delivery system that has a safety valve.

21. The device of claim 19, wherein the pulse oximeter has a probe, a housing, and a microprocessor.

22. A portable device, comprising:
a housing comprising a gas cartridge housing one or more doses of a gas, a mouthpiece for delivering the gas to the subject, a non-invasive probe for measuring the gas in the blood at a peripheral body site, a microprocessor for displaying the signal and a read-out screen for displaying the results of the analysis, wherein the signal provides a measurement of gas saturation values measured based on a factor of time of administration of the gas to the measurement taken at the peripheral body site.

* * * * *